United States Patent [19]

Thominet et al.

[11] Patent Number: 4,816,471

[45] Date of Patent: Mar. 28, 1989

[54] SUBSTITUTED HETEROCYCLIC BENZAMIDES, METHODS OF PREPARING THEM AND THEIR APPLICATION AS ANTI-EMETICS

[75] Inventors: Michel Thominet, Paris; Jacques Acher, Itteville; Jean-Claude Monier, Lardy, all of France

[73] Assignee: Societe d'Etudes Scientifiques et Industrielles de l'Ille-de France, Paris, France

[21] Appl. No.: 858,906

[22] Filed: Apr. 30, 1986

Related U.S. Application Data

[63] Continuation of Ser. No. 620,946, Jun. 15, 1984, abandoned, which is a continuation-in-part of Ser. No. 395,994, Jul. 7, 1982, abandoned, which is a continuation of Ser. No. 5,191, Jan. 22, 1979, abandoned.

[30] Foreign Application Priority Data

Jan. 20, 1978 [FR] France ................... 78 01633
Nov. 7, 1978 [FR] France ................... 78 31458

[51] Int. Cl.⁴ .................... A61K 31/40; A61K 31/41; C07D 207/09
[52] U.S. Cl. .................... 514/428; 514/359; 548/259; 548/567
[58] Field of Search ............ 514/408, 428, 359; 548/567, 259,

[56] References Cited

U.S. PATENT DOCUMENTS

| | | | |
|---|---|---|---|
| 3,342,826 | 9/1967 | Miller et al. | 424/274 |
| 3,577,440 | 5/1971 | Lunsford et al. | 424/274 |
| 3,862,139 | 1/1975 | Podesva et al. | 548/567 |
| 3,891,671 | 6/1975 | Thominet | 548/567 |
| 4,029,673 | 6/1977 | Bulteau et al. | 548/567 |
| 4,039,672 | 8/1977 | Bulteau et al. | 514/359 |
| 4,097,487 | 6/1978 | Murakami et al. | 548/567 |
| 4,158,060 | 6/1979 | Kaplan et al. | 424/274 |
| 4,172,143 | 10/1979 | Kaplan et al. | 548/567 |
| 4,279,822 | 7/1981 | Cale et al. | 548/557 |
| 4,294,828 | 10/1981 | Thominet et al. | 548/567 |
| 4,330,472 | 5/1982 | Ogata et al. | 548/567 |

FOREIGN PATENT DOCUMENTS 1364231 8/1974 United Kingdom .

*Primary Examiner*—Joseph Paul Brust
*Attorney, Agent, or Firm*—Fitzpatrick, Cella, Harper & Scinto

[57] ABSTRACT

There are provided substituted heterocyclic benzamides and derivatives thereof which exhibit strong anti-emetic properties.

24 Claims, No Drawings

SUBSTITUTED HETEROCYCLIC BENZAMIDES, METHODS OF PREPARING THEM AND THEIR APPLICATION AS ANTI-EMETICS

This application is a continuation of application Ser. No. 620,946 filed June 15, 1984, now abandoned, which in turn, is a continuation-in-part of application Ser. No. 395,994 filed July 7, 1982, now abandoned, which in turn is a continuation of application Ser. No. 005,191, filed Jan. 22, 1979, now abandoned.

BACKGROUND OF THE INVENTION

This invention relates to compounds which are useful as pharmaceutical agents, and methods for making them. The compounds of the present invention act on the nervous system so as to inhibit vomiting; that is, they are anti-emetics.

These compounds belong to the general class of compounds known as benzamides. More particularly, these compounds can be described as substituted heterocyclic benzamides. The novel compounds of the present invention are characterized by especially high anti-emetic activities as compared with prior art known compounds.

DETAILED DESCRIPTION OF THE INVENTION

The invention relates to new substituted heterocyclic benzamides, their salts of addition with pharmacologically acceptable acids, their quaternary ammonium salts, their N-oxides and their optically active isomers, of formula (I):

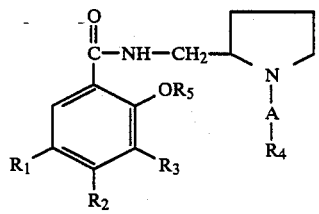

(I)

wherein:
R$_4$ is a C$_{3-8}$ cycloalkyl or C$_{5-8}$ cycloalkenyl group
A is a C$_{1-3}$ alkylene group
R$_5$ is a C$_{1-3}$ alkyl group
R$_1$ is a halogen atom, a sulfamoyl, C$_{1-3}$ alkylsulfamoyl, C$_{1-3}$ dialkylsulfamoyl, C$_{1-3}$ alkylsulfonyl or C$_{1-3}$ alkylsulfinyl group
R$_2$ is a hydrogen or halogen atom, an amino or C$_{1-3}$ alkoxy group or is joined with R$_1$ to form an azimido group.
R$_3$ is a hydrogen or C$_{1-3}$ alkoxy group, with the proviso that when R$_4$ is a C$_{3-8}$ cycloalkyl group and R$_2$ is a hydrogen atom, then R$_3$ is a C$_{1-3}$ alkoxy group.

In a second embodiment the invention includes substituted heterocyclic benzamides of Formula 1 wherein R$_4$ is a C$_{3-8}$ cycloalkyl group and especially where:
A is a methylene group
R$_5$ is a methyl group
R$_1$ is a sulfamoyl, C$_{1-2}$ alkylsulfamoyl, C$_{1-2}$ alkylsulfonyl or C$_{1-2}$ alkylsulfinyl group
R$_2$ is a hydrogen atom, a methoxy or amino group
R$_3$ is a hydrogen atom or a methoxy group with the proviso that when R$_2$ is hydrogen, R$_3$ is methoxy.

In another embodiment the invention includes substituted heterocyclic benzamides of Formula 1 wherein R$_4$ is a C$_{5-8}$ cycloalkenyl group and, particularly where:
A is a methylene group
R$_1$ is a sulfamoyl, C$_{1-3}$ alkylsulfamoyl, C$_{1-3}$ alkylsulfinyl or C$_{1-3}$ alkylsulfonyl group
R$_5$ is a methyl group
R$_2$ is a hydrogen atom or an amino group
R$_3$ is a hydrogen atom or a methoxy group.

Particularly useful compounds of the present invention are those saturated tri-substituted forms which are described by the above mentioned general Formula I, wherein:
R$_4$ is a C$_{3-8}$ cycloalkyl group;
A is a methylene group;
R$_1$ is a sulfamoyl, C$_{1-3}$ alkylsulfamoyl, C$_{1-3}$ alkylsulfinyl, or C$_{1-3}$ alkylsulfonyl group;
R$_2$ is a hydrogen atom, an amino group, a C$_{1-3}$ alkoxy group or is joined with R$_1$ to form an azimido group;
R$_3$ is a C$_{1-3}$ alkoxy group, if R$_2$ is a hydrogen atom, but if R$_2$ is not a hydrogen atom, then R$_3$ is a hydrogen atom; and
R$_5$ is a C$_{1-3}$ alkyl group For convenience, these compounds may be referred to as the compounds of Formula II.

Similarly, the inventors now find that another class of the compounds of the present invention, which can be called the "unsaturated, di- or tri-substituted" forms are also especially useful. These compounds are also of the above mentioned general Formula I, wherein:
R$_4$ is a C$_{5-6}$ cycloalkenyl group;
A is a methylene group;
R$_1$ is a sulfamoyl, C$_{1-3}$ alkylsulfamoyl, C$_{1-3}$ alkylsulfinyl or C$_{1-3}$ alkylsulfonyl;
R$_2$ is a hydrogen atom, an amino group, a C$_{1-3}$ alkoxy group or is joined with R$_1$ to form an azimido group;
R$_3$ is a hydrogen atom if R$_2$ is not a hydrogen atom, but if R$_2$ is a hydrogen atom, then R$_3$ is a hydrogen atom or a C$_{1-3}$ alkoxy group; and
R$_5$ is a C$_{1-3}$ alkyl group.

These compounds are also referred to herein as compounds of Formula III. For each of the compounds of Formulas I, II and III, the terms "saturated" or "unsaturated" refer to the R$_4$ substituent and the terms "di-substituted" or "tri-substituted" refer to the degree of substitution on the benzene ring of the R$_1$, R$_2$, R$_3$ and R$_5$ substituents.

The invention also includes salts of addition to the pharmacologically acceptable acids, quaternary ammonium salts, oxides and levorotatory and dextrorotatory isomers of the compounds of Formula (I), (II) and (III).

The compounds of the invention are prepared by reacting an acid of the Formula (IV):

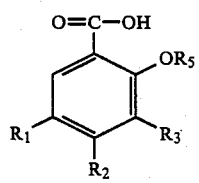

(IV)

wherein R$_1$, R$_2$, R$_3$ and R$_5$ are defined as above, or one of its reactive derivatives such as its acid halide, alkyl ester, reactive ester such as its methoxy methyl ester or cyanomethyl ester, aromatic ester, N-hydroximide ester, symmetrical anhydride or mixed anhydride, formed e.g. from a carbonic acid ester or a haloformic ester, or its azide, hydrazide, azolide, acid isothiocyanate, trichloroacetophone, or triphenylphosphine derivative, with an amine of the Formula (V):

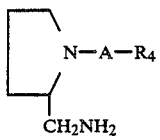

(V)

wherein A and R₄ are defined as above, or one of its reactive derivatives such as the derivative obtained by reacting the amine with a phosphorus chloride, the phosphorus oxychloride, a dialkyl, diaryl or ortho-phenylenechlorophosphite, an alkyl or aryldichlorophosphite, an isothiocyanate of the amine, a sulphamide or a substituted urea. The invention is not limited to derivatives of the acid and amine mentioned above.

The amidifying reaction may be carried out in situ or when the intermediate derivative has been isolated.

It is also possible to react the free acid and the free amine in the presence of a condensing agent such as silicon tetrachloride, trichlorophenylsilane, phosphoric anhydride, a carbodiimide or an alkoxyacetylene to obtain pharmacologically useful compounds.

The Formula (I) compounds may equally be prepared by reacting the Formula (IV) acid or one of its reactive derivatives defined as above, with a dihaloalkylamine of the Formula (VI):

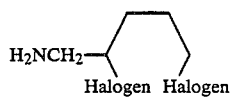

(VI)

wherein the halogen is a chlorine, bromine or iodine atom, then by reacting the compound obtained, of the Formula (VII):

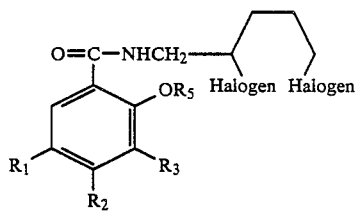

(VII)

with an amine of the Formula (VIII):

$$H_2N-A-R_4 \quad (VIII)$$

wherein R₄ and A are defined as above.

The methods of preparing the compounds according to the invention are set out in the following diagram:

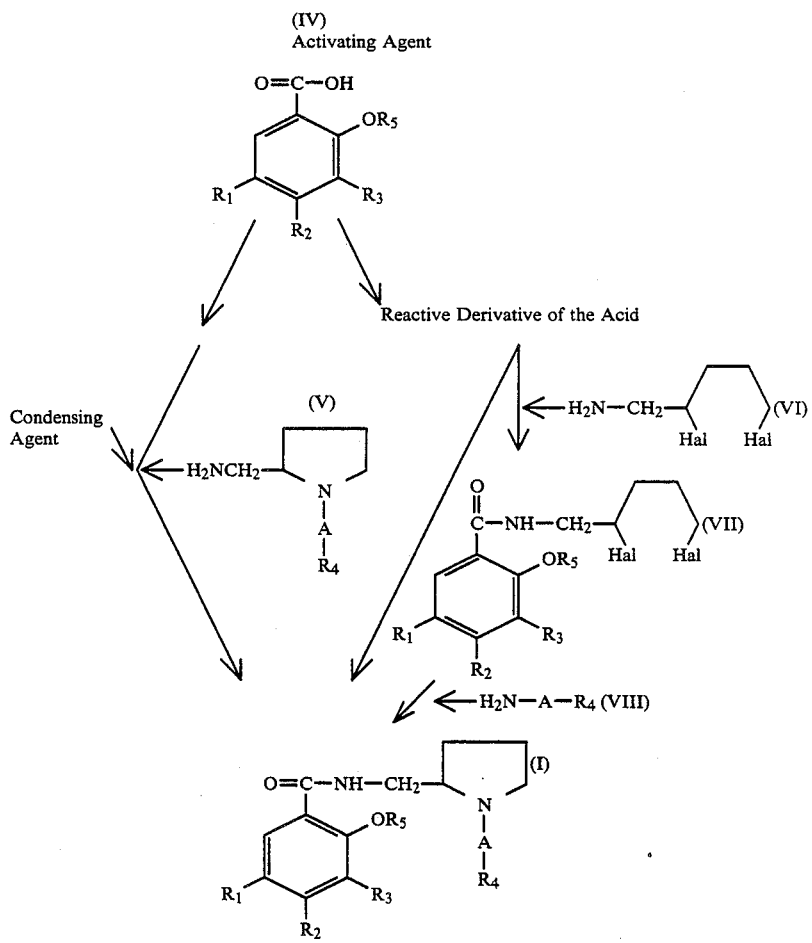

The amidifying reactions may be conducted with or without the use of solvent. A solvent, if used, should be relatively inert with regard to the amidifying reaction.

Examples of such solvents are alcohols, polyols, ketones, benzene, toluene, dioxan, chloroform and diethyleneglycol dimethyl ether. It is also possible to use an excess of the amine used as raw material as the solvent. It may be preferable to heat the reaction mixture during amidification, for example to the boiling point of the above mentioned solvents.

The compounds obtained by the method of the invention may, if necessary, be reacted with pharmaceutically acceptable inorganic or organic acids such as hydrochloric, hydrobromic, sulphuric, phosphoric, oxalic, acetic, tartaric, citric or methane-sulphonic acids, to give acid addition salts.

Similarly, these compounds may be reacted with alkyl sulphates or halides to give quaternary ammonium salts. Also, they may be oxidized in a conventional manner, (e.g. with hydrogen peroxide and manganese dioxide) to give the corresponding N-oxide.

Some examples will now be given to illustrate the technical features of the invention. It should be understood that these examples are offered only for the purposes of illustrating the present invention and to enable one skilled in the art to practice the invention. They are not intended to limit or define the invention. Rather, it is intended that the scope of the invention be limited only by the claims appended hereto.

EXAMPLE 1

N-(1-cyclopropylmethyl 2-pyrrolidinylmethyl)-2-methoxy 4-amino 5-ethylsulphinyl benzamide 2-methoxy 4-amino 5-ethylsulphinyl benzoic acid 149 g of 2-methoxy 4-amino 5-ethylthio benzoic acid and 260 ml of acetic acid are introduced into a 1 liter flask. After heating to 80° C., the mixture is cooled to 50° C., then a solution of 66 ml of 111 volumes hydrogen peroxide in 130 ml of acetic acid is added in fractions, while maintaining the temperature at 45°–50° C. by light cooling.

The resulting solution is left at room temperature for 2 days, then filtered and concentrated under vacuum.

The oily residue is dissolved in 500 ml of water and 20% ammonia, under light heating. After filtration in the presence of charcoal, the acid is precipitated by addition of 20% sulphuric acid until pH=4.

The resulting crystals are drained, washed with water until $SO_4^=$ ions have disappeared and dried at 50° C.

120 g of 2-methoxy 4-amino 5-ethylsulphinyl benzoic acid is obtained (M.P.=158° C.—yield=75%).

125 g of 2-methoxy 4-amino 5-ethylsulphinyl benzoic acid, 490 ml of chloroform and 52 g of triethylamine are introduced into a 2 l flask provided with a stirrer, a thermometer and a dropping funnel.

The mixture is cooled to 0° C., then 56 g of ethylchloroformate is added dropwise under cooling so as to keep the temperature between 0° and 5° C. The mixture is stirred 1 hour at 5° C., then 81.5 g of 1-cyclopropyl-methyl 2-aminomethyl pyrrolidine is added dropwise between 5° and 10° C. The mixture is stirred 1 hour at 5° C. then at room temperature. The solution is then treated with water and hydrochloric acid.

The chloroformic phase is decanted and extracted three times with acidified water. The aqueous solutions are joined together and filtered in presence of charcoal. After addition of 220 g of potassium carbonate, the oily product which separates is decanted and extracted with methylene chloride. The organic solution is dried on potassium carbonate then methylene chloride is distilled off under vacuum. The residue is dissolved hot in 400 ml of ethyl acetate and the boiling solution is filtered in presence of charcoal. After cooling, the resulting crystals are drained, washed with ethyl acetate and ether, then dried.

The 146 g of product so obtained is recrystallized in 370 ml and 220 ml of methylethylacetone.

63 g of product is obtained which is dissolved in 300 ml of water and 16.5 ml of concentrated hydrochloric acid. The solution is filtered in presence of charcoal, then treated with 25 ml of 30% soda lye.

The resulting crystals are drained, washed with water and dried. 58 g of N-(1-cyclopropylmethyl 2-pyrrolidinylmethyl)-2-methoxy 4-amino 5-ethylsulphinyl benzamide is obtained (M.P.=157.5° C.–162° C.—yield=30%).

EXAMPLE 2

N-(1-cyclopropyl-methyl-2-pyrrolidinyl-methyl)-2-methoxy-4-amino-5-ethylsulphonyl-benzamide 2-methoxy-4-amino-5-ethylthiobenzoic acid 159 g of 2-methoxy-4-amino-5-mercaptobenzoic acid, 355 ml of water and 160 ml of soda lye are placed in a flask fitted with a condenser. The mixture is heated till the solids have dissolved, then 123 g of ethyl sulphate is added. The mixture is heated to reflux, treated with 10 ml of 30% of soda lye, then heated to reflux for 1 hour. It is cooled, 800 ml of water is added and the solution is filtered. The precipitate, obtained by adding 100 ml of concentrated hydrochloric acid in the presence of ether, is drained, washed with water and dried.

162 g of 2-methoxy-4-amino-5-ethylthiobenzoic acid is obtained (yield 88%).

2-methoxy-4-amino-5-ethylsulphonyl benzoic acid 123 g of 2-methoxy-4-amino-5-ethylthiobenzoic acid is dissolved hot in 542 ml of acetic acid. The solution obtained is cooled to 35° C., then 185 ml of 131 vol. hydrogen peroxide is added in small quantities and the temperature is raised to 80° C.

The temperature is lowered to 40° C. and the mixture is kept at that temperature for a few hours, then cooled to 10° C.

The precipitate formed is drained, washed with acetic acid and dried, then dissolved in 600 ml of water and 100 ml of 20% ammonia.

The precipitate formed by adding 70 ml of concentrated hydrochloric acid is cooled, drained, washed with water and dried.

61.5 g of hydrated 2-methoxy-4-amino-5-ethylsulphonyl benzoic acid is obtained (yield=42%—M.P.=95°-100° C.).

N-(1-cyclopropyl-methyl-2-pyrrolidinyl-methyl)-2-methoxy-4-amino-5-ethylsulphonyl-benzamide 31.3 g (0.31 mole) of triethylamine, 400 ml of tetrahydrofuran and 80.3 g (0.31 mole) of 2-methoxy-4-amino-5-ethylsulphonyl benzoic acid are placed in a 1 liter flask fitted with an agitator, a thermometer, a condenser and a dropping funnel. A rubbery precipitate is formed which gradually crumbles. After 30 minutes at room temperature it is cooled to 0° C. and 33.6 g (0.31 mole) of ethyl chloroformate is added drop by drop.

This is kept under agitation for 1 hour between 0° and 5° C. and 62 g (0.40 mole) of 1-(cyclopropyl-methyl)-2-amino-methyl-pyrrolidine is added drop by drop while the temperature is kept at the same level. A thick precipitate is formed. The reaction medium is agitated for a further 2 hours at room temperature then left to stand overnight. The crystals obtained are filtered, washed twice with 100 ml of tetrahydrofuran and dried in an oven at 50° C. 137 g of product is obtained and is dissolved with boiling water. After filtering and drying, 91 g (74.3%) of crystals is obtained; these are recrystallized in 600 ml of 90% alcohol. They are filtered, washed twice with 50 ml of alcohol and dried in an oven at 40° C. 81.5 g (yield 66.5%) of N-(1-cyclopropylmethyl-2-pyrrolidinyl-methyl)-2-methoxy-4-amino-5-ethylsulphonyl benzamide is obtained, melting at 181° C.

| Analyses | Calculated | Found |
|---|---|---|
| S % | 8.11 | 8.06 |

EXAMPLE 3

N-(1-cyclopropylmethyl 2-pyrrolidinyl methyl)-2-methoxy 4-amino 5-methylsulphamoyl benzamide 156 g of 2-methoxy 4-amino 5-methylsulphamoyl benzoic acid, 138 ml of water and 60.5 g of triethylamine are introduced into a 2 l flask provided with a stirrer, a condenser, a thermometer and a dropping funnel. The mixture is stirred, then 350 ml of acetone is added. After cooling to 0° C., 65 g of ethyl chloroformate is added dropwise between 0° and 5° C. The mixture is stirred for 30 minutes between 0° and 5° C., then 100 g of 1-cyclopropylmethyl 2-aminomethyl pyrrolidine is added dropwise between 5° and 10° C.

The mixture is stirred for 1 hour between 5° and 10° C., then for 30 minutes at room temperature.

The acetone is distilled off under vacuum, then the residue is treated with 600 ml of water and 50 ml of acetic acid. The precipitate is drained and dissolved in 4 l of water. The solution is filtered in presence of charcoal, then made alkaline with 20% ammonia.

The precipitate is drained, washed with water and dried at 55° C.

164 g of product is obtained which is dissolved in 400 ml of boiling 95% alcohol. The solution is filtered in presence of charcoal. After cooling, the crystals are drained, washed with alcohol and dried at 50° C.

127 g of N-(1-cyclopropylmethyl 2-pyrrolidinylmethyl)-2-methoxy 4-amino 5-methylsulphamoyl benzamide is obtained (M.P.=173°-174° C.—yield=53%).

EXAMPLE 4

N-(1-cyclopropylmethyl-2-pyrrolidinylmethyl)-2,3-dimethoxy-5-sulphamoyl benzamide 2,3-dimethoxy-5-sulphamoyl benzoyl chloride 419 g (1.6 mole) of 2,3-dimethoxy-5-sulphamoyl benzoic acid and 1,351 g (11.35 moles) of thionyl chloride are placed in a 2 liter flask fitted with an agitator, a thermometer and a condenser connected to a soda bubbler. The mixture is brought to reflux for 1 hour, after which the excess thionyl chloride is expelled under vacuum. The residue is dissolved in 1,000 ml of hexane, filtered, washed twice with 500 ml of petroleum ether and dried in a desiccator under vacuum. 424 g (yield 94.8%) of 2,3-dimethoxy-5-sulphamoyl benzoyl chloride is obtained with a melting point of 153° C.

N-(1-cyclopropyl-methyl-2-pyrrolidinyl-methyl)-2,3-dimethoxy-5-sulphamoyl benzamide 20 g (0.13 moles) of 1-cyclopropyl-methyl-2-amino-methylpyrrolidine and 150 ml of methyl-ethyl-ketone are placed in a 500 ml flask fitted with an agitator, a thermometer and a condenser. 36.3 g (0.13 mole) of 2,3-dimethoxy-5-sulphamoyl benzoyl chloride is also introduced in stages and the temperature is kept between 15° and 20° C. The thick paste obtained is diluted with 170 ml of water and reacted for 1 hour at ambient temperature. It is then evaporated dry and the residue is dissolved in 200 ml of water and made alkaline with an excess of ammonia. The base is precipitated and crystallizes slowly. The crystals are filtered, washed with water and dried in an oven at 50° C. 50 g (yield 97%) of N-(1-cyclopropyl-methyl-2-pyrrolidinyl-methyl) 2,3-dimethoxy-5-sulphamoyl benzamide is obtained. This is re-crystallized three times in butyl acetate, and 26 g (50.5%) of crystals is obtained. The crystals are dissolved in normal hyrochloric acid, filtered, made alkaline with normal soda and re-filtered. They are washed with water until the Cl-ions have completely disappeared and dried in an oven (50° C.), to give 24 g (46.6%) of crystals which melt at 136° C. (they are insoluble in water).

| Analyses | Calculated | Found |
|---|---|---|
| S % | 8.06 | 8.13 |

EXAMPLE 5

N-(1-cyclopropylmethyl 2-pyrrolidinylmethyl)-2,3-dimethoxy 5-methylsulphamoyl benzamide 113 g of 2,3-dimethoxy 5-methylsulphamoyl benzoic acid, 450 ml of acetone and 41.5 g of triethylamine are introduced into a 2 l flask provided with a stirrer, a thermometer and a dropping funnel. The solution is cooled to 5° C., then 44.5 g of ethyl chloroformate is added dropwise between 5° and 10° C. The mixture is stirred for 30 minutes at 10° C., then 66 g of 1-cyclopropylmethyl 2-aminomethyl pyrrolidine is added dropwise between 10° and 15° C. The mixture is stirred 1 hour at 15° C. then 1 hour at room temperature.

The suspension is treated with water and the acetone is distilled off. The residue is treated with 1 l of water and acidified with sulphuric acid. The solution is filtered in presence of charcoal and made alkaline with 20% ammonia.

The crystals are drained, washed with water, dried at 40° C., dissolved again in acidified water and precipitated with 20% ammonia.

138 g of product is obtained which is dissolved in 290 ml of boiling ethyl acetate. The solution is filtered in presence of charcoal. After cooling, the crystals are drained, washed with ethyl acetate, dried at 40° C. and then dissolved in acid medium. The solution is filtered and made alkaline. The crystals are drained, washed and dried.

110 g of N-(1-cyclopropylmethyl 2-pyrrolidinylmethyl)-2,3-dimethoxy 5-methylsulphamoyl benzamide is obtained (M.P.=110.5°-111.5° C. yield=65%).

EXAMPLE 6

N-(1-cyclohexenyl-methyl-2-pyrrolidylmethyl)-2,3-dimethoxy 5-sulphamoyl benzamide 13 g of 2,3-dimethoxy-5-sulphamoyl-benzoic acid (0.05 mole), 150 ml of acetone, 35 ml of water and 5 g of triethylamine (0.05 mole) are placed in a 500 ml flask fitted with an agitator, a thermometer, a condenser and a dropping funnel. The mixture is cooled to between 0° and +5° C. and 5.5 g of ethyl chloroformate (0.05 mole) is poured in drop by drop. The reaction medium is agitated until the precipitate is completely dissolved, then re-cooled to 0° C. and 9.7 g of 1-(1-cyclohexenyl)-methyl-2-aminomethylpyrrolidine (0.05 mole) is poured in drop by drop.

The medium is reacted for 5 hours at room temperature then left to stand. The solvents are evaporated under vacuum and the residue is dissolved in 150 ml of hydrochloric acid (density 1.18). An insoluble oil is decanted off, then the aqueous solution is made alkaline with 13 ml of ammonia (density 0.91). The precipitate formed is filtered, washed with water and re-crystallized in 120 ml of isopropanol. 6.1 g of product is obtained and is re-crystallized in 250 ml of isopropanol. Yield=4.5 g (21%). M.P.=169° C.

EXAMPLE 7

N-(1-cyclobutylmethyl 2-pyrrolidinylmethyl)-2-methoxy 4-amino 5-ethylsulphonyl benzamide 155.4 g of 2-methoxy 4-amino 5-ethylsulphonyl benzoic acid, 600 ml of acetone and 60.6 g of triethylamine are introduced into a 3 l flask provided with a stirrer, a thermometer and a dropping funnel.

The mixture is stirred for 15 minutes. The suspension is cooled to 15° C., then 65.1 g of ethyl chloroformate is added dropwise. The mixture is then left to react for 1 hour 15 minutes at room temperature then cooled again to 15° C. and 100.8 g of 1-cyclobutylmethyl 2-aminomethyl pyrrolidine is added dropwise. The mixture is left to react for 2 hours at room temperature, then the precipitate is drained, washed with acetone, dried at 50° C., then treated with 1 l of water, drained, washed with water and dried at 50° C. 167 g of product is obtained which is recrystallized in 2 l of acetone and dried at 50° C.

128 g of N-(1-cyclobutylmethyl 2-pyrrolidinylmethyl)-2-methoxy 4-amino 5-ethylsulphonyl benzamide is obtained (M.P.=170° C.—yield=52%).

EXAMPLE 8

N-(1-cyclohexylmethyl-2-pyrrolidinyl-methyl)-2-methoxy-4-amino-5-ethylsulphonyl-benzamide 25.9 g of 2-methoxy-4-amino-5-ethylsulphonyl benzoic acid, 40 ml of water, 200 ml of acetone and 13.9 ml of triethylamine (density 0.726) are placed in a 500 ml flask fitted with an agitator, a thermometer and a dropping funnel. The solution is cooled to about 0° to 5° C. and 10.9 g of ethyl chloroformate is dripped in. The mixture is agitated for 40 minutes at about 0° C., then 19.6 g of 1-cyclohexyl-methyl-2-aminomethyl pyrrolidine is added drop by drop. The mixture is agitated for 2 hours at room temperature then left to stand. The acetone is evaporated under vacuum and the residue is dissolved in 100 ml of water and 25 ml of acetic acid and filterd in the presence of vegetable black. The filtrate is made alkaline with 100 ml of 40% soda lye. A precipitate is formed; this is filtered, washed with plenty of water and dissolved moist in 230 ml of boiling acetone. The hot solution is filtered in the presence of vegetable black and the filtrate is crystallized. The product is drained, washed with a little acetone and dried in an oven at 50° C.

25 g (57%) of product is collected: melting point 155° C.

EXAMPLE 9

N-(1-cyclopentylmethyl 2-pyrrolidinylmethyl)-2-methoxy 4-amino 5-ethylsulphonyl benzamide 91 g of 2-methoxy 4-amino 5-ethylsulphonyl benzoic acid, 365 ml of acetone and 36 g of triethylamine are introduced into a 2 l flask provided with a stirrer, a thermometer and a dropping funnel. The suspension is cooled to 0° C., then 38 g of ethylchloroformate are added dropwise under cooling so as to keep the temperature between 0° and 5° C. The mixture is stirred 30 minutes at 5° C., then 64 g of 1-cyclopentylmethyl 2-aminomethyl pyrrolidine are added dropwise between 5° and 10° C. The triethylamine hydrochloride is then drained and washed with acetone. The acetone is distilled off under vacuum and the residue is dissolved in 1 l of water and 32 mll of concentrated hydrochloric acid. The solution is filtered in presence of charcoal and made alkaline with 20% ammonia. The precipitate is drained, washed with water and dried at 50° C.

134 g of product is obtained which is dissolved hot in 270 ml of ethyl acetate. The boiling solution is filtered in presence of charcoal, then cooled. The crystals are drained, washed with ethyl acetate and dried at 50° C.

107 g of product is obtained which is dissolved in 220 ml of absolute alcohol, then a solution of 9.2 g of dry hydrochloric acid in 63 ml of absolute alcohol is added. The crystals are drained, washed with alcohol and ether, dried at 50° C., then dissolved in 660 ml of water. The solution is filtered in presence of charcoal and made alkaline with 20% ammonia. The resulting product is dissolved in methylene chloride and the organic solution is decanted and dried on potassium carbonate. The methylene chloride is then distilled off under vacuum and the residue is dissolved in 195 ml of hot ethyl acetate. After cooling, the crystals are drained, washed with hot ethyl acetate and dried at 50° C.

97 g of product is obtained which is recrystallized in 190 ml of acetonitrile.

82 g of N-(1-cyclopentylmethyl 2-pyrrolidinylmethyl)-2-methoxy 4-amino 5-ethylsulphonyl benzamide is obtained (M.P.=140°–141° C.—yield=55%).

EXAMPLE 10

N-(1-cyclopentylmethyl 2-pyrrolidinylmethyl)-2-methoxy 4-amino 5-ethylsulphonyl benzamide N-(2,5-dichloropentyl)-2-methoxy 4-amino 5-ethylsulphonyl benzamide 121.5 g of 2-methoxy 4-amino 5-ethylsulphonyl benzoic acid, 400 ml of chloroform and 47.5 g of triethylamine are introduced into a 2 l flask provided with a stirrer, a condenser, a thermometer and a dropping funnel.

The solution is cooled to 0° C., then 51 g of ethyl chloroformate is added dropwise with the temperature being kept below 10° C.

91 g of dichloropentylamine, 400 ml of chloroform and 47.5 g of triethylamine are introduced into a 3 l flask provided with a stirrer, a condenser, a thermometer and a dropping funnel.

The chloroformic solution of the mixed anhydride previously obtained is added dropwise to the solution so obtained, between 20° and 25° C.

The mixture is then left overnight, then treated with water. The aqueous phase is decanted and the chloroformic phase washed with water, then dried on sodium sulphate.

The chloroform is distilled off under vacuum, then the residue is treated with 400 ml of absolute alcohol. The resulting crystals are drained, washed with alcohol and dried at 50° C.

138 g of N-(2,5-dichloropentyl)-2-methoxy 4-amino 5-ethylsulphonyl benzamide is obtained (M.P.=109°–110° C.—yield=74%).

N-(1-cyclopentenylmethyl 2-pyrrolidinylmethyl)-2-methoxy 4-amino 5-ethylsulphonyl benzamide 98 g of 1-aminomethylcyclopentene and 100 g of N-(2,5-dichloropentyl) 2-methoxy 4-amino 5-ethylsulphonyl benzamide are introduced into a 500 ml flask provided with a stirrer, a condenser and a thermometer.

The suspension is stirred for 5 hours at 40° C., then heated in an oven at 40° C. for 40 hours. The mixture is then treated with 500 ml of water and 150 ml of acetic acid. The resulting solution is filtered in presence of charcoal then made alkaline with 20% ammonia. The crystals are drained, washed with water and dried.

80 g of product is obtained which is dissolved in 160 ml of boiling absolute ethanol. The solution is filtered in presence of charcoal. After cooling, the crystals are drained, washed with actone, dried and recrystallized in 104 ml of absolute ethanol.

The crystals are drained, washed with ethanol and dried at 50° C.

48 g of N-(1-cyclopentenylmethyl 2-pyrrolidinylmethyl)-2-methoxy 4-amino 5-ethylsulphonyl benzamide is obtained (M.P.=125°–126° C.—yield=45%).

EXAMPLE 11

N-[1-(1-cyclohexenylmethyl)-2-pyrrolidinylmethyl]-2-methoxy 4-amino 5-ethylsulphonyl benzamide, phosphate 72.5 g of 2-methoxy 4-amino 5-ethylsulphonyl benzoic acid, 200 ml of acetone and 28.3 g of triethylamine are introduced into a 1 l flask provided with a stirrer, a thermometer, a cooler and a dropping funnel. The mixture is then cooled to 0°–5° C. and 30.4 g of ethylchloroformate is added drop by drop.

The medium is reacted for 30 minutes at 5° C., then 55.2 g of 1-(1-cyclohexenylmethyl)-2-aminomethyl pyrrolidine is added drop by drop.

After 1 hour 30 minutes at room temperature, the mixture is filtered and the filtrate evaporated under vacuum. The residual oil is treated with 500 ml of water and hydrochloric acid.

After addition of soda lye, the suspension is extracted three times with 300 ml of methylene chloride. The organic solution is washed three times with 100 ml of water, then dried on magnesium sulphate, filtered and evaporated under vacuum.

The residue is treated with 350 ml of ethanol and the resulting crystals are then filtered, washed with ethanol and dried at 60° C.

The compound so obtained is dissolved in 450 ml of boiling ethanol. The solution is filtered in presence of charcoal and the filtrate is acidified with a solution of 21.7 g of orthophosphoric acid in 50 ml of ethanol.

After cooling, the precipitate is filtered and dried at 50° C., then dissolved in boiling methanol. The solution is filtered in presence of charcoal. After cooling, the crystals are filtered, washed with methanol and dried at 50° C.

57 g of N-[1(1-cyclohexenylmethyl)-2-pyrrolidinylmethyl]-2-methoxy 4-amino 5-ethylsulphonyl benzamide, phosphate is obtained (M.P.=192° C.—yield=38%).

EXAMPLE 12

N-(1-cyclohexenylmethyl 2-pyrrolidinylmethyl) 2,3-dimethoxy 5-methylsulphamoyl benzamide 133 g of 2,3-dimethoxy 5-methylsulphamoyl benzoic acid, 550 ml of acetone and 49 g of triethylamine are introduced into a 2 l flask provided with a stirrer, a condenser, a thermometer and a dropping funnel. The mixture is cooled to 5° C., then 52.5 g of ethyl chloroformate is added dropwise under cooling so as to keep the temperature between 5° and 10° C.

The mixture is then stirred for 30 minutes and 94 g of 1-cyclohexenylmethyl 2-aminomethyl pyrrolidine is added dropwise at room temperature.

After stirring for 1 hour, the precipitate is drained and washed with acetone.

The filtrate is concentrated under vacuum to constant weight, then the residue is dissolved in water containing acetic acid. The solution is filtered in presence of charcoal, then made alkaline with 20% ammonia. The oily product is decanted and extracted with methylene chloride. The resulting solution is dried on potassium carbonate and methylene chloride is then distilled off under vacuum to constant weight.

The residue is dissolved in 440 ml of absolute ethanol and the solution is acidified with 40 ml of concentrated hydrochloric acid. The resulting crystals are drained, washed with ethanol and dried at 50° C.

The 176 g of product so obtained is dissolved in hot water. The solution is filtered in presence of charcoal, then made alkaline with 20% ammonia.

The precipitate is drained, washed with water, dried in an oven at 55° C. and recrystallized in 306 ml of ethyl acetate.

134 g of N-(1-cyclohexenylmethyl 2-pyrrolidinylmethyl) 2,3-dimethoxy 5-methylsulphamoyl benzamide is obtained (M.P.=120°–121° C.—yield=61%).

EXAMPLE 13

N-(1-cycloheptenylmethyl 2-pyrrolidinylmethyl) 2-methoxy 5-methylsulphamoyl benzamide N-(2,5-dichloropentyl) 2-methoxy 5-methylsulphamoyl benzamide 210 g of 2-methoxy 5-methylsulphamoyl benzoic acid, 715 ml of chloroform and 86 g of triethylamine are introduced into a 3 l flask provided with a stirrer, and condenser, a thermometer and a dropping funnel.

The solution is cooled to 5° C., then 91.5 g of ethyl chloroformate is added dropwise over 20 minutes between 5° and 10° C.

The mixture is then stirred for 30 minutes between 12° and 20° C.

162 g of 2,5-dichloropentylamine hydrochloride, 715 ml of chloroform and 86 g of triethylamine are introduced into a 4 l flask provided with a stirrer, a condenser, a thermometer and a dropping funnel. The mixture is stirred till dissolution, then the chloroformic solution of mixed anhydride previously prepared is added dropwise.

The mixture is stirred until the carbon dioxide release ceases, then the chloroform is concentrated and the residue is treated with water.

Resulting crystals are drained, washed with water and dried at 40° C.

312 g of N-(2,5-dichloropentyl) 2-methoxy 5-methylsulphamoyl benzamide is obtained (M. P. =120°-121° C.−yield=95%).

79.5 of N-(2,5-dichloropentyl) 2-methoxy 5-methylsulphamoyl benzamide and 104 g of 1-cycloheptenylmethyl amine are introduced into a 500 ml flask.

The resulting suspension is heated to 60° C., then treated with water. The precipitate is drained, washed with water and dried at 40° C.

The 66 g of product so obtained is dissolved in water and acetic acid, then the solution is filtered in the presence of charcoal and made alkaline with 20% ammonia. The precipitate is drained, washed with water, dried at 50° C. and then recrystallized in 146 ml of absolute ethanol.

56 g of N-(1-cycloheptenylmethyl 2-pyrrolidinylmethyl) 2-methoxy 5-methylsulphamoyl benzamide is obtained (M. P. =148°-149° C.-yield=62%).

EXAMPLE 14

N-[1(1-cyclohexenylmethyl) 2-pyrrolidinylmethyl]2-methoxy 5-sulphamoyl benzamide 56.3 g of 1-(1-cyclohexenylmethyl)-2-aminomethyl pyrrolidine and 300 ml of methylethylacetone are introduced into a 3 l flask provided with a stirrer, a thermometer, a cooler and a dropping funnel.

The mixture is cooled to 15° C., then a solution of 92 g of an 80% 2-methoxy 5-sulphamoyl benzoyl chloride in 1500 ml of methylethylacetone is added drop by drop. The medium is reacted for 1 hour, then the precipitate is filtered and dried at 50° C. The resulting compound is treated with 1500 ml of water. Then the suspension is filtered and the solid residue is treated with 1000 ml of water and 500 ml of ammonia (d=0.90). The mixture is heated for one hour under reflux, then cooled and the resulting compound is filtered, washed with water and dried at 60° C. 43 g of product is obtained.

The aqueous filtrate resulting from the filtration of the suspension is treated with 500 ml of ammonia (d=0.90), then heated for one hour under reflux. The precipitate is extracted with 1200 ml of methylene chloride, then the organic solution is dried and evaporated under vacuum. 44 g of product is obtained.

The 87 g of product is then dissolved in 400 ml of boiling ethanol. The solution is filtered in presence of charcoal, then cooled.

The resulting crystals are filtered, washed with ethanol and dried at 50° C.

62 g of N-[1-(1-cyclohexenylmethyl)-2-pyrrolidinylmethyl]2-methoxy 5-sulphamoyl benzamide is obtained (M. P.=167° C.−yield=52%).

EXAMPLE 15

N-(1-cyclohexenylmethyl 2-pyrrolidinylmethyl) 2-methoxy 5-methylsulphamoyl benzamide 174 g of 1-cyclohexenylmethylamine and 150.5 g of N-(2,5-dichloropentyl) 2-methoxy 5-methylsulphamoyl benzamide are introduced into a 1 l flask provided with a stirrer, a condenser and a thermometer.

The mixture is heated to 80° C. for 6 hours then treated with 1500 ml of water and 150 ml of 30% soda lye. The oily product is extracted with methylene chloride, the organic solution is dried on potassium carbonate and methylene chloride is distilled off.

The amine in excess is then distilled off under vacuum, and the residue is dissolved in 630 ml of absolute ethanol and 55 g of fumaric acid.

The resulting crystals are drained, washed with absolute ethanol and dried at 40° C.

The 97 g of product so obtained are dissolved in 500 ml of hot water and the solution is made alkaline with 20% ammonia. After cooling, the precipitate is drained, washed with water, dried at 40° C. and recrystallized twice in isopropanol and absolute ethanol.

The 51 g of product so obtained is dissolved in 260 ml of water and 10 ml of concentrated hydrochloric acid. The solution is filtered and made alkaline with 20% ammonia. The precipitate is drained, washed with water and dried at 40° C.

50.5 g of N-(1-cyclohexenylmethyl 2-pyrrolidinylmethyl)-2-methoxy 5-methylsulphamoyl benzamide is obtained (M. P.=140°-141° C.−yield=29.5%).

EXAMPLE 16

N-(1-cyclopropylmethyl 2-pyrrolidinylmethyl) 2,3-dimethoxy 5-ethylsulphonyl benzamide, hydrochloride 2,3-dimethoxy 5-chlorosulphony benzoic acid 1620 ml of chlorosulphonic acid is introduced in a 3 l flask provided with a stirrer, a condenser and a thermometer. Then 146 g of 2,3-dimethoxy benzoic acid is added portionwise, between 10° and 15° C. The mixture is stirred for 4 hours between 22° and 28° C., then left overnight at room temperature.

The solution is then poured dropwise into a 10 l flask containing 600 g of crushed ice.

The flask is cooled on the outside and additionally crushed ice is introduced together with the sulphochloride so as to keep the temperature between 0° and 5° C.

The resulting precipitate is drained, washed with water and dried.

184 g of 2,3-dimethoxy 5-chlorosulphonyl benzoic acid is obtained (M. P.=152°-153° C.−yield=82%).

2,3-dimethoxy 5-ethylsulphonyl benzoic acid 660 ml of water, 124 g of sodium sulphite and 165 g of sodium bicarbonate are introduced into a 6 l flask provided with a stirrer a condenser and a thermometer.

The mixture is heated to 70°-80° C., then the 184 g of 2,3-dimethoxy 5-chlorosulphonyl benzoic acid are added gradually.

The solution is heated for 2 hours, at 70°-80° C., then it is cooled to 20° C. and 33 ml of soda lye, 760 ml of absolute ethanol and 307 g of ethyl iodide are added. The mixture is heated to reflux for 35 hours, then 163 ml of soda lye are added and the mixture is heated to reflux for 2 additional hours. The alcohol is distilled off under vacuum and the residue is treated with 1.3 l of water.

The solution is filtered in presence of charcoal and acidified with concentrated hydrochloric acid.

The precipitate is drained, washed with water and dried at 60° C.

138 g of 2,3-dimethoxy 5-ethylsulphonyl benzoic acid is obtained (M. P.=138°–139° C.—yield=77%).

2,3-dimethoxy 5-ethylsulphonyl benzoyl chloride 44 g of thionyl chloride and 25 g of 2,3-dimethoxy 5-ethylsulphonyl benzoic acid are introduced into a 250 ml flask provided with a condenser.

The mixture is heated to 40° C., then cooled and 26 g of 2,3-dimethoxy 5-ethylsulphonyl benzoic acid is added. The mixture is heated again to 40° C. until dissolution, then heated to reflux.

The thionyl chloride is distilled off under vacuum. 55 g of 2,3-dimethoxy 5-ethylsulphonyl benzoyl chloride is obtained (M. P.=67°–68° C., yield=100%).

N-(1-cyclopropylmethyl 2-pyrrolidinylmethhyl) 2,3-dimethoxy 5-ethylsulphonyl benzamide, hydrochloride 29 g of 1-cylcopropylmethyl 2-aminomethyl pyrrolidine and 105 ml of chloroform are introduced into 1 l flask provided with a stirrer, a thermometer and a dropping funnel, then a solution of 55 g of 2,3-dimethoxy 5-ethylsulphonyl benzoyl chloride in 108 ml of chloroform is added dropwise while keeping the temperature between 5° and 10° C.

The mixture is then stirred for 2 hours at room temperature, the chloroform is distilled off and the residue is dissolved in acidified water.

The solution is filtered in presence of charcoal, then made alkaline with 20% ammonia. The oily product is extracted with methylene chloride and the organic solution thus obtained is dred on potassium carbonate. The methylene chloride is distilled off under vacuum.

76 g of product is obtained which is dissolved in 132 ml of absolute ethanol and treated with a solution of 7 g of hydrochloric acid gas in 20 ml of absolute ethanol. The precipitate is drained, washed with ethanol and dried at 45°–50° C., then recrystallized in 112 ml of 98% alcohol.

The product is drained, washed and dried at 45° C.

52 g of N-(1-cyclopropylmethyl 2-pyrrolidinylmethyl)2,3-dimethoxy 5-ethylsulphonyl benzamide, hydrochloride is obtained (M. P.=167°–170° C.—yield=62%).

EXAMPLE 17

N-(1-cyclohexylmethyl-2-pyrrolidinyl-methyl)-2,3-dimethoxy-5-sulphamoyl benzamide 26.1 g of 2,3-dimethoxy-5-sulphamoyl-benzoic acid (0.10 mole), 40 ml of water, 200 ml of acetone and 10.1 g of triethylamine (0.10 mole) are placed in 500 ml flask fitted with an agitator, a thermometer and a dropping funnel. The solution is cooled to between 0° and +5° C. and 10.9 g of ethyl chloroformate (0.10 mole) is added drop by drop. It is agitated for 1 hour 30 minutes with the temperature kept at about +5° C., then 19.6 g of 1-cyclohexylmethyl-2 aminomethyl pyrrolidine (0.10 mole) is added drop by drop. A precipitate forms progressively as more and more is added. The reaction medium is then agitated at room temperature, after which it is left to stand. The crystals are filtered, washed three times with water then with 100 ml of 10% ammonia and dried in an oven at 50° C. 50 g is obtained.

The product is dissolved in 300 ml of water and 10 ml of acetic acid, the solution is filtered and the filtrate is rendered alkaline with 20 ml of ammonia (density 0.91). It is crystallize in refrigerator, filtered, washed with water and dried in an oven at 50° C. 28.5 g of product is obtained. Yield: 65%. M. P.: 189° C.

EXAMPLE 18

N-(1-cycloheptyl-methyl-2-pyrrolidinyl methyl)-2-methoxy-4-amino-5-methyl-sulphamoyl benzamide 6.5 g of 2-methoxy-4-amino-5-methyl sulphamoyl benzoic acid, 75 ml of acetone, 14 ml of water and 3.5 ml of triethylamine (density 0.726) are placed in a 250 ml flask fitted with an agitator, a thermomter, a condenser and a dropping funnel. The solution is cooled to between 0° and +5° C. and 2.7 g of ethyl chloroformate is added drop by drop. The reaction medium is agitated for 45 minutes at room temperature then cooled to 0° C. again. 6.8 g of 1-cycloheptyl methyl-2-amino methyl pyrrolidine is added drop by drop. The medium is reacted for 2 hours then left to stand. The solvents are expelled and the solid residue dissolved in 50 ml of water and 20 ml of hydrochloric acid (density 1.18).

The suspensin obtained is made alkaline with ammonia. It is extracted 3 times with 50 ml of methylene chloride. The organic phase is washed twice with 50 ml of water, dried over magnesium sulphate and filtered. The filtrate is evaporated to dryness under vacuum. The residue is dissolved in 80 ml of water and 20 ml of hydrochloric acid (density 1.18). The hydrochloride crystallizes. It is drained, washed with water and dried in an oven at 50° C.

7 g of product is obtained, with a melting point of about 230° C.

It is re-crystallized in 300 ml of ethanol.

4.3 g (35%) of benzamide hydrochloride is obtained, with a melting point of 228° C.

EXAMPLE 19

N-(1-cycloheptyl methyl-2-pyrrolidinyl methyl)-2-methoxy- 4-amino-5-ethyl sulphonyl benzamide 4.9 g of 2methoxy-4-amino-5-ethyl sulphonyl benzoic acid, 57 ml of acetone, 10 ml of water and 2.6 ml of triethylamine (density 0.726) are placed in a 250 ml flask fitted with an agitator, a thermometer, a condenser and a dropping funnel. The solution is cooled to between 0° and +5° C. and 2.1 g of ethyl chloroformate is added drop by drop. The reaction medium is agitated for 45 minutes at room temperature then cooled to 0° C. and 5.3 g of 1-cycloheptyl methyl-2-amino methyl pyrrolidine is poured in drop by drop. The medium is agitated for 4 hours then left to stand overnight. The solvents are evaported to dryness and the residue is dissolved in 60 ml of water and 15 ml of hydrochloric acid (density 1.18). Extraction is carried out 3 times with 50 ml of methylene chloride, the organic phase is dried over magnesium sulphate and filtered, and the solvent is evaporated under vacuum. The residue is dissolved in 100 ml of water. The solution is filtered in the presence of carbon black and the filtrate is made alkaline with about 7 ml of ammonia (density 0.91). A gum is precipitated. It is extracted 3 times with 50 ml of methylene chloride. The organic phase is washed twice with 50 ml of water, dried over magnesium sulphate and filtered. The solvent is evaporated under vacuum and the residue is re-crystallized in 100 ml of isopropanol.

4.5 g (52%) of product is obtained, with a melting point of 156° C.

EXAMPLE 20

N-(1-cyclopropylmethyl-2-pyrrolidinyl methyl)-2,4-dimethoxy-5-methyl-sulphonyl benzamide

2,4-dimethoxy-5-chlorosulphonyl benzoic acid 1,800 ml of chlorosulphonic acid is placed in a 4 liter flask fitted with an agitator and a thermometer, and is cooled to 10° C. 328 g of finely powdered 2,4-dimethoxy benzoic acid is added in stages in the course of 45 minutes, between 10° and 15° C. The acid dissolves gradually as it is introduced. When all the acid has been added the solution is gradually heated to 55° C. and that temperature is maintained for 5 hours. The solution is left to stand overnight, then poured very slowly into 17 kg of ice, with agitation and with external cooling. The acid which is precipitated is drained, washed with water and dried in air.

456 g of product is obtained. The yield is 90%.

2,4-dimethoxy-5-methylsulphonyl benzoic acid 930 ml of water, 208 g of sodium sulphite and 277 g of sodium bicarbonate are placed in a 6 liter flask fitted with a sealed agitator, reflux condenser and a thermometer. They are heated to 70°–80° C. and 309 g of 2,4-dimethoxy-5-chlorosulphonyl benzoic acid is added gradually.

A large amount of $CO_2$ is given off simultaneously with the dissolving of the acid. The acid takes 45 minutes to introduce. Heating is continued for a further 2 hours at 70°–80° C. to complete the reaction. The pH of the solution is about 7.

220 ml of 30% soda lye, 1,120 ml of absolute alcohol and 470 g of methyl iodide are added to the reaction mixture and it is heated with a gentle reflux. After 3 hours 30 minutes a weight loss of 50 g is noted and the solution is found to be only very slightly alkaline with phenolphthalein.

50 g of methyl iodide and 110 ml of soda lye are added and the medium is heated to reflux again. The initial reflux temperature rises progressively to 65° C. then to 75° C. Another weight loss is observed but the solution remains alkaline. Heating is continued for 8 hours altogether.

500 ml of alcohol is then distilled off. The residue is dissolved in 2 liters of water and the mineral salts dissolved. The solution obtained, which is slightly turbid, is filtered with charcoal. The 2,4-dimethoxy-5-methylsulphonyl benzoic acid is precipitated by adding concentrated hydrochloric acid until it turns Congo red. It is drained, washed with water and dried at 60° C.

255 g of product is obtained (89%).

2,4-dimethoxy-5-methyl-sulphonyl-benzoyl chloride 161 g of 2,4-dimethoxy-5-methyl sulphonyl-benzoic acid is reacted. 590 g of thionyl chloride, 5 drops of dimethylformamide and about half of the organic acid are placed in a 2 liter flask fitted with a reflux condenser. The resultant suspension is heated in a water bath at 55° C. for about 5 minutes. The second half of the organic acid is added and heating is continued for 20 minutes at 60°–65° C. then for 45 minutes at 70°–75° C. The medium becomes fluid and turns yellow. The acid dissolves gradually, while the acid chloride begins to crystallize. When the reaction is over the excess thionyl chloride is distilled to constant weight, finishing up under vacuum.

169 g (98%) of acid chloride is obtained. This melts with decomposition at 200° C.

N-(1-cyclopropyl methyl-2-pyrrolidinyl methyl)-2,4-dimethoxy-5-methyl sulphonyl benzamide 74 g of 1-cyclopropylmethyl-2-aminomethyl-pyrrolidine and 460 ml of chloroform are placed in a liter flask fitted with an agitator and a thermometer. 134 g of finely powdered 2,4-dimethoxy-5-methylsulphonyl benzoyl chloride is added gradually. The temperature is kept between 5° and 10° C. by cooling in an iced bath. Each portion of acid chloride dissolves immediately. It takes 1 hour to introduce. Agitation is then continued for 1 hour at 5° C. then for 1 hour at room temperature.

The solution obtained is dissolved in 1 liter of water and the chloroform is distilled off. This leaves in suspension a light precipitate which is drained, washed and dried. 6 g of 2,4-dimethoxy-5-methylsulphonyl benzoic acid is recovered in this way (M. P.=208°–310° C.).

The aqueous solution is then made alkaline by adding 20% ammonia until it turns phenolphthalein. Ether is present to aid in crystallizing the base. The product is drained, washed with water and dried at 45° C.

153 g (81%) of product is obtained, with a melting point of 193°–196° C.

After re-crystallizing in 900 ml of acetonitrile, 133 g of benzamide is collected, with a melting point of 190°–191° C. Total yield 70%.

EXAMPLE 21

N-(1-cycloheptylmethyl-2-pyrrolidinylmethyl)-2,3-dimethoxy-5-sulphamoyl benzamide 13 g of 2,3-dimethoxy-5-sulphamoyl benzoic acid, 150 ml of acetone, 28 ml of water and 7 ml of triethylamine (density 0.726) are placed in a 250 ml flask fitted with an agitator, a thermometer, a condenser and dropping funnel. The resultant solution is cooled from 0° to +5° C. 5.4 g of ethyl chloroformate is added drop by drop and the reaction medium is agitated for 45 minutes at room temperature and cooled to 0° C. again. 13.7 g of 1-cycloheptylemthyl-2-aminomethyl-pyrrolidine is added drop by drop. The medium is agitated for 1 hour at room temperature then left to stand. The crystals formed are drained, washed with water and dried in an oven at 30° C.

Yield 22.3 g (98%). M. P. 180° C.

The product is re-crystallized in 400 ml of isopropanol.

14.3 g (63%) of amide is collected, melting at 180° C.

EXAMPLE 22

N-(1-cyclohexenylmethyl 2-pyrrolidinylmethyl) 2-methoxy 4,5-azimido benzamide 60 g of 5-carbomethoxy 6-methoxy benzotriazole, 14 ml of water 62 g of 1-cyclohexnylmethyl 2-aminomethyl pyrrolidine are introduced into a 500 ml flask provided with a condenser.

The mixture is heated at 90°–95° C. for 10 hours, then treated with water and acetic acid. The solution is filtered in the presence of charcoal, then made alkaline with 20% ammonia. The precipitate is drained, dried, ground and poured in water and then drained again, washed and dried at 50° C.

The resulting product is dissolved in water and acetic acid and the solution is made alkaline with 20% ammonia. The precipitate is drained, washed with water, dried in an oven at 50° C. and recrystallized twice in 225 ml and 220 ml of absolute ethanol respectively.

65 g of N-(1-cyclohexenylmethyl 2-pyrrolidinylmethyl) 2-methoxy 4,5-azimido benzamide is obtained (M.P.=150.5°-151.5° C. yield=60%).

EXAMPLE 23

N-(1-cyclopentylmethyl 2-pyrrolidinyl methyl)-2-methoxy 4-amino 5-ethylsulphinyl benzamide, fumarate 90 g of 2-methoxy 4-amino 5-ethylsulphinyl benzoic acid, 370 ml chloroform and 38 g of triethylamine are introduced into a 2 l flask provided with a stirrer, a condenser, a thermometer and a dropping funnel. The solution is cooled to 0° C., then 40 g of ethyl chloroformate is added dropwise, under cooling, so as to keep the temperature between 0° and 5° C. The mixture is then stirred for 1 hour between 0° and 5° C.

68 g of 1-cyclopentylmethyl 2-aminomethyl pyrrolidine is added dropwise between 5° and 10° C. and then the mixture is stirred for 1 hour at room temperature.

After addition of water, the chloroform is distilled off and the aqueous solution is then filtered in the presence of charcoal and made alkaline with 20% ammonia.

The oily product is extracted with methylene chloride, the organic solution is washed with water and dried on potassium carbonate, then the methylene chloride is distilled under vacuum. 145 g of product is obtained.

139 g of the base previously obtained are dissolved hot in 360 ml of methanol and 39.5 g of fumaric acid. After cooling, the crystals are drained, washed with methanol and dried at 50° C.

The 104 g of fumarate so obtained are recrystallized in methanol.

73 g of N-(1-cyclopentylmethyl 2-pyrrolidinylmethyl) 2-methoxy 4-amino 5-ethylsulphinyl benzamide fumarate is obtained (M.P.=183°-184° C.−yield=39%).

EXAMPLE 24

N-[1-(2-cyclopropyl ethyl) 2-pyrrolidinylmethyl]-2-methoxy 4-amino 5-ethylsulphonyl benzamide, phosphate 85.5 g of 2-methoxy 4-amino 5-ethylsulphonyl benzoic acid, 850 ml of acetone and 120 ml of water are introduced into a 2 l flask provided with a stirrer, a thermometer, a cooler and a dropping funnel.

The solution is cooled, then 33.5 g of triethylamine is added.

The mixture is cooled to 0° C., then 46.2 g of isobutyl chloroformate is added dropwise. The mixture is left to react for 20 minutes, then 59 g of 1-(2-cyclopropylethyl)-2-aminomethyl pyrrolidine is added at 0° C.

The mixture is left to react at room temperature, then a solution of 45 ml of 40% soda lye in 200 ml of water is added.

The organic solvent is evaporated and the aqueous suspension is extracted three times with 200 ml of methylene chloride. The organic phase is dried on magnesium sulphate, filtered and evaporated under vacuum.

The oily residue is dissolved at 50° C. in 700 ml isopropanol then 40 g of orthophosphoric acid is added. The precipitate is filtered and recrystallized in 1200 ml of methanol. After recrystallization in 900 ml of methanol, 88 g of N-[1-(2-cyclopropylethyl) 2-pyrrolidinylmethyl]-2-methoxy 4-amino 5-ethylsulphonyl benzamide, phosphate is obtained (M.P.=209° C.−yield=53%).

The products of the invention can be administered in any number of conventional forms such as capsules, tablets, pills, in granulated form or as an injectable solution. Many methods for compounding these preparations are well-known in the art. Substances which are inert relative to the compounds of the invention can be used in these preparations, such as lactose, magnesium stearate, starch, talc, cellulose, levilite, alkali metal lauryl-sulphates, saccharose and other vehicles commonly employed in pharmaceutical preparations.

The compounds may be administered in doses of 50-750 mg per day taken in 1 or more stages.

The examples which follow illustrate several pharmaceutical preparations, each made in a conventional manner from the compounds of the invention.

EXAMPLE 25

| tablets | |
|---|---|
| N—(1-cyclopropylmethyl-2-pyrrolidinylmethyl 2,3-dimethoxy-5-sulphamoyl benzamide | 100 mg |
| dried starch | 20 mg |
| lactose | 100 mg |
| methylcellulose 1500 cps | 1.5 mg |
| levilite | 10 mg |
| magnesium stearate | 4 mg |
| for 1 tablet. | |

EXAMPLE 26

| capsules | |
|---|---|
| N—(1-cyclopropylmethyl-2-pyrrolidinylmethyl) 2-methoxy-4-amino-5-ethylsulphonyl benzamide | 50 mg |
| microcrystalline cellulose | 50 mg |
| methylcellulose 1500 cps | 1 mg |
| magnesium stearate | 5 mg |
| talc | 2 mg |
| for 1 capsule. | |

EXAMPLE 27

| injectable solution | |
|---|---|
| N—(1-cyclopropylmethyl-2-pyrrolidinylmethyl) 2,3-dimethoxy-5-sulphamoyl benzamide | 40 mg |
| 1N hydrochloric acid | 0.10 ml |
| sodium chloride | 14 mg |
| for 2 ml | |

EXAMPLE 28

| injection solution | |
|---|---|
| N—(1-cyclopropylmethyl-2-pyrrolidinylmethyl) 2-methoxy-4-amino-5-ethylsulphonyl benzamide | 100 mg |
| 1N hydrochloric acid | 0.250 ml |
| sodium chloride | 8 mg |
| for 2 ml | |

To prepare the tablets, the selected compound is mixed with the starch and lactose by the method of successive dilutions; the mixture is granulated with methylcellulose. The levilite, magnesium stearate and talc are added to the granules before proceeding with compression.

It is possible to replace the methylcellulose with any other appropriate granulating agent, such as ethylcellulose, polyvinylpyrrolidone or starch paste. The magnesium stearate may be replaced by stearic acid.

When preparing injectable solutions, it is possible to dissolve the compound of the invention in the following acids: hydrochloric or levulinic acid, gluconic acid, or glucoheptonic acid. The solution is prepared under sterile conditions and made isotonic with an alkali metal chloride such as sodium chloride, then preservatives are added. It is also possible to prepare the same solution without adding any preservatives: the ampoule is then filled under nitrogen and sterilized for ½ hour at 100° C.

EXAMPLE 29

The pharmacodynamic tests on the compounds of this invention, and particularly a study of their anti-emetic power have shown strong activity on the nervous system as apomorphine antagonists. This has been demonstrated by observing the anti-emetic power relative to apomorphine in dogs by the method of Chen and Ensor. In accordance with the above-mentioned procedures, the compounds of the invention were administered subcutaneously 30 minutes before the administration of apomorphine, which was administered subcutaneously in a dose of 100 ug/kg. The results of these tests are set forth in the following Table 1:

TABLE 1

| Compound of Example # | $ED_{50}$ µg/kg |
| --- | --- |
| 1 | 0.70 |
| 2 | 0.40 |
| 3 | 0.40 |
| 4 | 2.20 |
| 5 | 0.50 |
| 6 | 2.80 |
| 8 | 2.00 |
| 10 | 1.30 |
| 11 | 0.57 |
| 12 | 1.15 |
| 13 | 0.50 |
| 14 | 0.85 |
| 15 | 0.21 |
| 16 | 0.08 |
| 22 | 2.00 |

| Prior Art Compounds | Results Reported in U.S. Pat No. 4,172,143[o] |
| --- | --- |
| *SLC-036 | 37.0 |
| **77205 | 14.0 |
| ***77149 | 40.0 |

*N—(1-cyclopropylmethyl 2-pyrrolidinylmethyl)-2-methoxy-5-sulphamoyl benzamide
**N—(1-cyclohexylmethyl 2-pyrrolidinylmethyl)-2-methoxy-5-sulphamoyl benzamide
***N—(1-cyclopropylmethyl 2-pyrrolidinylmethyl)-2-methoxy-5-dimethylsulphamoyl benzamide
[o]method of administration believed oral Compounds SLC-036, 77205 and 77149 are disclosed in U.S. Pat. No. 4,172,143 for comparison purposes, as Examples 10, 33 and 37 therein. The results for those compounds are reported in Table IX of the '143 Patent and are believed to represent results from oral administration.

EXAMPLE 30

Pharmacological tests were carried out under oral administration to determine anti-emetic $ED_{50}$ in accordance with the procedure of Example 29 with the following results:

TABLE 2

| Example No. | $ED_{50}$ (oral) µg/kg |
| --- | --- |
| 2 | 0.90 |
| 14 | 1.20 |
| 15 | 1.10 |
| 16 | 0.23 |
| SLC-036 | 37.00 |
| 77205 | 14.00 |
| 77149 | 40.00 |

EXAMPLE 31

The acute toxicity of the compounds of the invention has been studied in the mouse. The $LD_{50}$'s are set out in the following Table 3. From this data it can be seen that the lethal dose of the claimed compounds are far greater than the effective dose. This characteristic is highly desirable because the possibility of toxic effects due to the administration of therapeutic doses is thereby minimized.

TABLE 3

| Compound Of Example # | MODE OF ADMINISTRATION | | | |
| --- | --- | --- | --- | --- |
| | I.V. (Intravenous) | S.C. (Subcutaneous) | I.P. (Intraperitoneal) | P.O. (Oral) |
| 2 | 52.5–54.6 | 380–396 | 203.5–220 | 1260–1325 |
| 4 | 60–64.5 | 930 | 372–403 | 2280 |
| 6 | 96 | — | 60% at 240 mg/kg | — |
| 8 | 37–40.8 | 336–342 | 133–145.2 | 348–380 |
| 10 | 41.8–42 | 330–360 | 203.5–211.5 | 980–990 |
| 11 | 29.5–31.8 | 343–360 | 180–181 | 510–555 |
| 12 | 57.8–62 | 297–319 | 198–200 | 540–560 |
| 13 | 45.5–48 | 322.5–336 | 128–139.5 | 312.5–330 |
| 14 | 82.5–85.5 | 630–640 | 294–316.8 | 525–542.5 |
| 15 | 44.2–46.5 | 462–494 | 204–208 | 540–558 |
| 16 | 92.9–97.2 | 595–597 | 303–338 | 588–598 |

EXAMPLE 32

The neurological activity of the compounds of the invention was compared to the activity of prior art compounds in U.S. Pat. No. 4,172,143 and with a standard in this field, Sulpiride, N-[(1-ethylpyrrolidinyl-2)methyl]-2-methoxy-5 sulphamoyl benzamide. The compounds were tested for antagonism to chewing stereotypes induced by apomorphine (1.25 mg/kg in rats, according to the method of Janssen in Arzn. Forsch. 1960-10, 1003–5, under subcutaneous administration and the results were as follows:

TABLE 4

| Compound of Example No. | $ED_{50}$ (mg/kg) |
| --- | --- |
| 6 | 40.0 |
| 8 | 33.0 |
| 11 | 13.7 |
| 12 | 4.0 |
| 13 | 1.5 |
| 14 | 16.4 |
| 15 | 1.22 |
| 16 | 3.2 |
| SLC-036 | 0% at 200 |
| 77205 | 20% at 200 |
| Sulpiride | 0% at 200 |

The compounds were also tested for antagonism to chewing stereotypes induced by dexamphetamine (10 mg/kg) in rats, by Janssen's method in Arzn. Forsch. 1961, 11, 932–938 under subcutaneous administration with the following results:

TABLE 5

| Compound of Example No. | ED$_{50}$ (mg/kg) |
| --- | --- |
| 8 | 15.4 |
| 10 | 14 |
| 11 | 5.4 |
| 12 | 1.5 |
| 13 | 0.54 |
| 14 | 10 |
| 15 | 0.78 |
| 16 | 1.34 |
| SLC-036 | 0% at 100 mg/kg |
| 77205 | 19 |
| Sulpiride | 0% at 100 mg/kg |

The compounds were also tested for potentiation of biting sterotypes induced by apomorphine (10 (mg/kg) in mice, under interperitoneal administration in accordance with Pedeson's method in *Brit J. Pharmacol.* 1968, 34 (1), 219–220 with the following results:

TABLE 6

| Compound of Example No. | ED$_{50}$ (mg/kg) |
| --- | --- |
| 2 | 1.6 |
| 6 | 2.6 |
| 12 | 0.33 |
| 16 | 0.25 |
| Sulpiride | 12% at 4 mg/kg. |

The compound of Example 2 was tested against sulpiride for potentiation of stereotypes induced by apomorphine (0.25 mg/kg) in rats under intraperitoneal administration with the following results:

TABLE 7

| Compound of Example No. | ED$_{50}$ (mg/kg) |
| --- | --- |
| 2 | 2.4 |
| Sulpiride | 30% at 8 mg/kg. |

What is claimed is:

1. Substituted heterocyclic benzamides, their salts of addition with pharmacologically acceptable acids, their non-toxic, pharmaceutically acceptable quaternary ammonium salts, their N-oxides and their optically active isomers, of Formula (I):

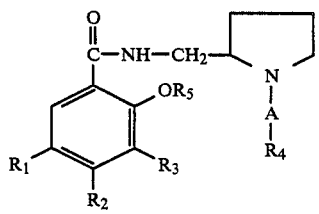

wherein:
- R$_4$ is a C$_{3-8}$ cycloalkyl
- A is a C$_{1-3}$ alkylene group
- R$_5$ is a C$_{1-3}$ alkyl group
- R$_1$ is a halogen atom, sulfamoyl, C$_{1-3}$ alkylsulfamoyl, C$_{1-3}$ dialkylsulfamoyl, C$_{1-3}$ alkylsulfonyl or C$_{1-3}$ alkylsulfinyl group
- R$_2$ is a hydrogen
- R$_3$ is an C$_{1-3}$ alkoxy group.

2. The substituted heterocyclic benzamides of claim 1 wherein:
- A is methylene group
- R$_5$ is a methyl group wherein:
- R$_1$ is sulfamoyl, C$_{1-2}$ alkylsulfamoyl, C$_{1-2}$ alkylsulfonyl or C$_{1-2}$ alkylsulfinyl group
- R$_2$ is a hydrogen atom
- R$_3$ is a methoxy group.

3. Substituted heterocyclic benzamides, their salts of addition with pharmcologically acceptable acids, their non-toxic, pharmaceutically acceptable quaternary ammonium salts, their N-oxides and their optically active isomers, of Formula (I):

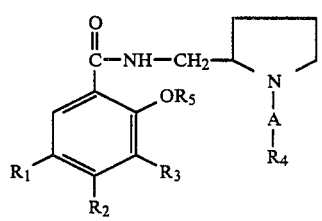

wherein:
- R$_4$ is a C$_{3-8}$ cycloalkyl or C$_{5-8}$ cycloalkenyl group
- A is a C$_{1-3}$ alkylene group
- R$_5$ is a C$_{1-3}$ alkyl group
- R$_1$ is a halogen atom, sulfamoyl, C$_{1-3}$ alkylsulfamoyl, C$_{1-3}$ dialkylsulfamoyl, C$_{1-3}$ alkylsulfonyl or C$_{1-3}$ alkylsulfinyl group
- R$_2$ is a hydrogen or halogen atom, amino or C$_{1-3}$ alkoxy group or is joined with R$_1$ to form an azimido group with the proviso that when R$_4$ is a C$_{3-8}$ cycloalkyl group, then R$_2$ is an amino group
- R$_3$ is a hydrogen or C$_{1-3}$ alkoxy group, with the proviso that when R$_3$ is alkoxy, R$_2$ is hydrogen.

4. The substituted heterocyclic benzamides of claim 3 wherein R$_4$ is a C$_{5-8}$ cycloalkenyl group.

5. The substituted heterocyclic benzamides of claim 4 wherein:
- A is a methylene group
- R$_5$ is a methyl group
- R$_1$ is sulfamoyl, C$_{1-2}$ alkylsulfamoyl, C$_{1-2}$ alkylsulfonyl or C$_{1-2}$ alkylsulfinyl group
- R$_2$ is a hydrogen atom, or amino group
- R$_3$ is a hydrogen atom or methoxy group.

6. The compound of claim 1 or 3 wherein:
- R$_4$ is a C$_{3-6}$ cycloalkyl
- A is a methylene group
- R$_1$ is sulfamoyl, C$_{1-3}$ alkylsulfamoyl, C$_{1-3}$ alkylsulfinyl, or C$_{1-3}$ alkylsulfonyl
- R$_5$ is a C$_{1-3}$ alkyl group.

7. The compound of claim 3 wherein:
- R$_4$ is a C$_{5-6}$ cycloalkenyl group
- A is a methylene group
- R$_1$ is sulfamoyl, C$_{1-3}$ alkylsulfamoyl, C$_{1-3}$ alkylsulfinyl, or C$_{1-3}$ alkylsulfonyl
- R$_5$ is a C$_{1-3}$ alkyl group.

8. The substituted heterocyclic benzamides of claim 3 wherein R$_4$ is a C$_{3-8}$ cycloalkyl group.

9. The substituted heterocyclic benzamides of claim 8 wherein:
- A is a methylene group
- R$_5$ is a methyl group
- R$_1$ is sulfamoyl, C$_{1-2}$ alkylsulfamoyl, C$_{1-2}$ alkylsulfonyl or C$_{1-2}$ alkylsulfinyl group
- R$_2$ is an amino group
- R$_3$ is a hydrogen atom.

10. Substituted heterocyclic benzamides, their salts of addition with pharmacologically acceptable acids, their non-toxic, pharmaceutically acceptable quaternary ammonium salts, their N-oxides and their optically active isomers, of Formula (I):

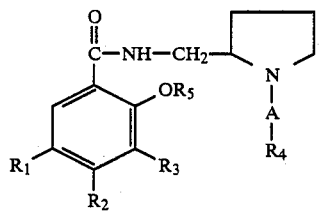

wherein:
- $R_4$ is a cyclopropyl group
- A is a methylene group
- $R_5$ is a methyl group
- $R_1$ is sulfamoyl, $C_{1-2}$ alkylsulfamoyl or $C_{1-2}$ alkylsulfonyl
- $R_2$ is a hydrogen atom
- $R_3$ is a methoxy group.

11. N-(1-cyclopropylmethyl 2-pyrrolidinylmethyl) 2-methoxy 4-amino 5-ethylsulfonyl benzamide.

12. N-(1-cyclopropylmethyl 2-pyrrolidinylmethyl) 2,3-dimethoxy 5-sulfamoyl benzamide.

13. N-(1-cyclohexylmethyl 2-pyrrolidinylmethyl) 2-methoxy 4-amino 5-ethylsulfonyl benzamide.

14. N-(1-cyclohexenylmethyl 2-pyrrolidinylmethyl) 2,3-dimethoxy 5-sulfamoyl benzamide.

15. N-(1-cyclohexenylmethyl 2-pyrrolidinylmethyl) 2-methoxy 5-methylsulfamoyl benzamide.

16. N-(1-cyclopropylmethyl 2-pyrrolidinylmethyl) 2,3-dimethoxy 5-ethylsulfonyl benzamide.

17. N-(1-cycloheptenylmethyl 2-pyrrolidinylmethyl) 2-methoxy 5-methylsulfamoyl benzamide.

18. N-(1-cyclohexenylmethyl 2-pyrrolidinylmethyl) 2,3-dimethoxy 5-methylsulfamoyl benzamide.

19. N-(1-cyclopentenylmethyl 2-pyrrolidinylmethyl) 2-methoxy 4-amino 5-ethylsulfonyl benzamide.

20. N-(1-cyclohexenylmethyl 2-pyrrolidinylmethyl) 2-methoxy 4-amino 5-ethylsulfonyl benzamide.

21. N-(1-cyclohexenylmethyl 2-pyrrolidinylmethyl) 2-methoxy 5-sulfamoyl benzamide.

22. A pharmaceutical composition having anit-emetic activity which comprises an effective amount to inhibit nausea of the compound of claims 1, 2, 4, 5, 6 7, 3, 10, 8 or 9 and a pharmaceutically acceptable carrier.

23. A process for the treatment of nausea in patients which comprises administering an effective amount to inhibit nausea of the compound of claims 1, 2, 4, 5, 6, 7, 3, 10, 8 or 9 and a pharmaceutically acceptable carrier.

24. A process for the treatment of neurological disorders in patients which comprises administering an amount effective to treat neurological disorders of the compound of claims 1, 2, 4, 5, 6, 7, 3, 10, 8 or 9 and a pharmaceutically acceptable carrier.

* * * * *